US00PP09826P

United States Patent [19]

Tas

[11] Patent Number: Plant 9,826

[45] Date of Patent: Mar. 11, 1997

[54] FERN PLANT NAMED 'GLOWSTAR'

[75] Inventor: Wim Tas, Aalsmeer, Netherlands

[73] Assignee: Milestone Agriculture Inc., Apopka, Fla.

[21] Appl. No.: 517,111

[22] Filed: Aug. 21, 1995

[51] Int. Cl.[6] ..... A01H 5/00

[52] U.S. Cl. ..... Plt./88.3

[58] Field of Search ..... Plt./88.3

*Primary Examiner*—James R. Feyrer

*Attorney, Agent, or Firm*—C. A. Whealy

[57] ABSTRACT

A distinct cultivar of Fern plant named Glowstar, characterized by its outwardly arching plant habit that is symmetrical in form; compact habit and low vigor; suitability for small pots; black rachis color; numerous pinnae per frond; short, narrow and finely serrated pinnae; and dark green and glossy pinnae.

1 Drawing Sheet

The present invention relates to a new and distinct cultivar of Fern plant, botanically known as *Pellaea falcata,* and hereinafter referred to by the cultivar name Glowstar.

The new cultivar was discovered by the inventor in Aalsmeer, Holland, as a naturally occurring mutation in a population of 100 plants of the species *Pellaea falcata.*

Asexual reproduction by tissue culture of the new cultivar at Aalsmeer, Holland, has shown that the unique features of this new Fern are stabilized and retained through more than twenty successive generations of asexual reproduction.

The new Fern has not been observed under all possible environmental conditions. The phenotype may vary somewhat with variations in environment such as temperature and light intensity, without, however, any variance in genotype. The following observations, measurements and comparisons describe plants grown in Apopka, Fla., under conditions generally used in commercial practice.

The following traits have been repeatedly observed and are determined to be the unique characteristics of Glowstar. These characteristics in combination distinguish Glowstar as a new and distinct cultivar:

1. Outwardly arching plant habit that is symmetrical in form.
2. Compact habit and low vigor.
3. Suitable for small pots.
4. Black rachis color.
5. Numerous pinnae per frond.
6. Short, narrow and finely serrated pinnae.
7. Dark green and glossy pinnae.

The new Fern is most similar to its parent cultivar, the species *Pellaea falcata.* The new Fern differs from the species *Pellaea falcata* in the following characteristics:

1. Plants of the new Fern have an outwardly arching plant habit that is symmetrical in form compared to the more upright and nonsymmetrical plant habit of plants of the species *Pellaea falcata.*

2. Plants of the new Fern are more compact and have a low vigor compared to plants of the species *Pellaea falcata.* The growth rate of plants of the species *Pellaea falcata* is twice as fast as the growth rate of plants of the new Fern.

3. Rachis length is longer on plants of the new Fern compared to plants of the species *Pellaea falcata,* however the rachis width is narrower.

4. Rachis color is darker on plants of the new Fern compared to plants of the species *Pellaea falcata.*

5. Pinnae are shorter, narrower, and more numerous on plants of the new Fern compared to plants of the species *Pellaea falcata.*

6. Pinnae margin is finely serrated on plants of the new Fern and entire on plants of the species *Pellaea falcata.*

7. Pinnae are ovate in shape on plants of the new Fern and obovate on plants of the species *Pellaea falcata.*

8. Pinnae are very glossy on plants of the new Fern whereas pinnae are dull and without gloss on plants of the species *Pellaea falcata.*

A detailed comparison of the new Fern and the species *Pellaea falcata* appears in Chart A at the end of the specification.

The accompanying colored photograph illustrates the overall appearance of the new cultivar, showing the colors as true as it is reasonably possible to obtain in colored reproductions of this type. The photograph comprises a top perspective view of a typical potted plant of Glowstar.

In the following description, color references are made to The Royal Horticultural Society Colour Chart except where general terms of ordinary dictionary significance are used. Measurements and numerical values represent averages for six typical plants.

Botanical classification: *Pellaea falcata* cultivar Glowstar.

Parentage: Naturally occurring sport or mutation of the species *Pellaea falcata.*

Propagation: By tissue culture.

Rooting habit: Rhizomes are creeping, fibrous and well-branched.

Plant description:

*Plant shape.*—Inverted triangle, symmetrical.

*Growth habit.*—Erect when young, becoming outwardly arching as fronds develop. Maintains compact size over time. Appropriate for small pots, 10 to 12.5-cm.

*Plant height.*—15 cm from soil line to top of plant plane.

*Plant width.*—21 cm in diameter.

*Plant vigor.*—Low.

*Crop time.*—24 weeks to finished 10-cm pot.

*Frond description.*—Leaf arrangement: One-pinnate. Frond length: 17.5 cm. Rachis length: 11 cm. Rachis width: 3.5 cm. Rachis color: Black, darker than 200A.

*Pinnae description.*—Pinnae shape: Ovate. Pinnae length: 19 mm. Pinnae width: 9 mm. Quantity of pinnae: 33 per frond. Margin: Finely serrated. Number of lobes: One at maturity. Pinnae tip: Acute, pointed. Pinnae base: Truncate. Pinnae aspect: Flat with margins slightly curled downward. Pinnae curl upwards at tip. Pinnae attachment: Petiolate. Petiole length: 1 mm. Pinnae texture: Glabrous, very glossy. Pinnae color: Immature, top side: 147A. Immature, under side: 147B. Mature, top side: 147A. Mature, under side: 147B. Venation pattern: Pinnate.

*Spores.*—Color, immature: 175A. Color, mature: 144C. Disease resistance: No resistance to disease has been noted. Slightly susceptible to Rhizoctonia sp.

| CHARACTERISTIC | CHART A 'Glowstar' | *Pallaea falcata* |
|---|---|---|
| PLANT SHAPE | Symmetrical | Not symmetrical |
| PLANT HABIT | Outwardly arching | Upright, not arching |
| PLANT SIZE | Compact | Large, vigorous |
| GROWTH RATE | Low | Rapid |
| CROP TIME, 10-cm pot | 24 weeks | 12 weeks |
| SUITABLE CONTAINER(S) | 10 to 12.5-cm pots | 10 to 20-cm pots |
| FROND SHAPE/ ARRANGEMENT | 1-pinnate | 1-pinnate |
| FROND LENGTH | 17.5 cm | 16.5 cm |
| RACHIS LENGTH | 11 cm | 7.5 cm |
| RACHIS WIDTH | 3.5 cm | 5.5 cm |
| RACHIS COLOR | Black, darker than 200A | Brown, 200A |
| QUANTITY OF PINNAE | 33 | 15 |
| PINNAE LENGTH | 19 mm | 27 mm |
| PINNAE WIDTH | 9 mm | 13.5 mm |
| PINNAE MARGIN | Finely serrated | Entire, not serrated |
| NUMBER OF LOBES | One at maturity at base, prominent | None |
| PINNAE SHAPE | Ovate | Obovate |
| PINNAE TIP | Acute, pointed | Acute, pointed |

-continued

| CHARACTERISTIC | CHART A 'Glowstar' | *Pallaea falcata* |
|---|---|---|
| PINNAE BASE | Truncate | Truncate |
| PINNAE ASPECT | Flat with margins slightly curled downward. Pinnae curl upwards at tip | Flat with margins slightly curled downwards. |
| PINNAE ATTACHMENT | Petiolate | Petiolate |
| PETIOLE LENGTH | 1 mm | 1.5 mm |
| PINNAE TEXTURE | Glabrous, very glossy | Glabrous, dull |
| PINNAE COLOR, IMMATURE, UPPER SIDE | 147A | 146A |
| PINNAE COLOR, IMMATURE, UNDER SIDE | 147B | 147B |
| PINNAE COLOR, MATURE, UPPER SIDE | 147A | 147A |
| PINNAE COLOR, MATURE, UNDER SIDE | 147B | 147B |

It is claimed:

1. A new and distinct cultivar of Fern plant named Glowstar, as illustrated and described.

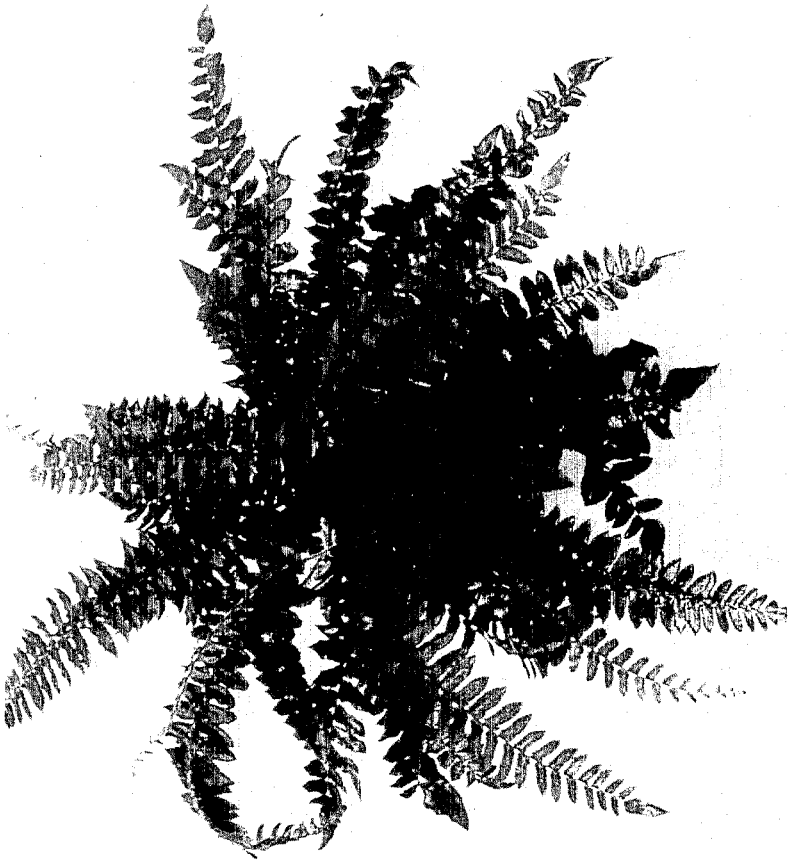

* * * * *